United States Patent [19]

Lovgren et al.

[11] Patent Number: 4,786,505
[45] Date of Patent: Nov. 22, 1988

[54] NEW PHARMACEUTICAL PREPARATION FOR ORAL USE

[75] Inventors: Kurt I. Lovgren, Mölnlycke; Ake G. Pilbrant, Kungsbacka, both of Sweden; Mitsuru Yasumura; Satoshi Morigaki, both of Hyogo, Japan; Minoru Oda, Ohita, Japan; Naohiro Ohishi, Fukuoka, Japan

[73] Assignee: Aktiebolaget Hassle, Sweden

[21] Appl. No.: 40,491

[22] Filed: Apr. 20, 1987

[30] Foreign Application Priority Data

Apr. 30, 1986 [GB] United Kingdom ............... 8610572

[51] Int. Cl.$^4$ .......................... A61K 9/22; A61K 9/32
[52] U.S. Cl. .................................... 424/468; 424/475; 424/479; 424/480; 424/482
[58] Field of Search ............... 424/480, 482, 468, 475, 424/479; 427/2, 3

[56] References Cited

U.S. PATENT DOCUMENTS 2,540,979 2/1951 Clymer et al. ..................... 167/82
4,685,919 8/1987 Amidon et al. ................... 427/2 X

FOREIGN PATENT DOCUMENTS

| 0005129 | 10/1979 | European Pat. Off. . |
| 1204363 | 8/1964 | Fed. Rep. of Germany . |
| 1617615 | 5/1966 | Fed. Rep. of Germany . |
| 2336218 | 5/1979 | Fed. Rep. of Germany . |
| 3046559 | 12/1980 | Fed. Rep. of Germany . |
| WO85/03436 | 8/1985 | PCT Int'l Appl. . |
| 1485676 | 9/1977 | United Kingdom . |

Primary Examiner—Michael Lusignan
Attorney, Agent, or Firm—Brumbaugh, Graves, Donohue & Raymond

[57] ABSTRACT

Pharmaceutical preparation containing omeprazole together with an alkaline reacting compound or an alkaline salt of omeprazole optionally together with an alkaline compound as the core material, one or more sub-coating layers comprising inert reacting compounds which are soluble or rapidly disintegrating in water, or polymeric, water soluble filmforming compounds, optionally containing pH-buffering alkaline compounds and an enteric coating as well as a process for the preparation thereof and the use in the treatment of gastrointestinal diseases.

14 Claims, No Drawings

NEW PHARMACEUTICAL PREPARATION FOR ORAL USE

FIELD OF THE INVENTION

The present invention is related to a new stable pharmaceutical preparation containing omeprazole for oral use, to a method for the manufacture of such a preparation and to a method of affecting gastric acid secretion and providing gastrointestinal cytoprotective effect when using them.

BACKGROUND OF THE INVENTION

From e.g. EP-A1-No. 0 005 129 omeprazole, 5-methoxy-2(((4-methoxy-3,5-dimethyl-2-pyridinyl)methyl)sulfinyl)-1H-benzimidazole, a potent inhibitor of gastric acid secretion is known. Omeprazole shows a powerful inhibitory action against secretion of gastric juice (Lancet, Nov. 27, 1982, p. 1223–1224) and can be used for the treatment of gastric and duodenal ulcers. Omeprazole is however susceptible to degradation/transformation in acid reacting and neutral media. The half-life of omeprazole in water solutions at pH-values less than four is shorter than ten minutes. Also at neutral pH-values the degration reaction proceeds rapidly, e.g. at pH=7 the half-life of omeprazole is about 14 hours, while at higher pH-values the stability in solution is much better (Pilbrant and Cederberg, Scand. J. Gastroenterology 1985; 20 (supp. 108) p. 113–120). The stability profile is similar in solid phase. The degradation of omeprazole is catalyzed by acidic reacting compounds and is stabilized in mixtures with alkaline reacting compounds. The stability of omeprazole is also affected by moisture and organic solvents.

From what is said about the stability properties of omeprazole, it is obvious that an oral dosage form of omeprazole must be protected from contact with the acid reacting gastric juice in order to reach the small intestine without degradation.

In human pharmacological studies it was found that the rate of release omeprazole from a pharmaceutical dosage form can influence the total extent of absorption of omeprazole to the general circulation (Pilbrant and Cederberg, Scand. J. Gastroenterology 1985; 20 (suppl. 108) p. 113–120). A fully bioavailable dosage form of omeprazole must release the active drug rapidly in the proximal part of the gastrointestinal canal.

In order to obtain a pharmaceutical dosage form of omeprazole which prevents omeprazole from contact with acidic gastric juice, the cores must be enteric coated. Ordinary enteric coatings, however, are made of acidic compounds. If covered with such a conventional enteric coating, omeprazole rapidly decomposes by direct or indirect contact with it, with the result that the preparations become badly discolored and lose in omeprazole content with the passage of time.

In order to enhance the storage stability the cores which contain omeprazole must also contain alkaline reacting constituents. When such an alkaline core is enteric coated with an amount of a conventional enteric coating polymer such as, for example, cellulose acetate phthalate, that permits the dissolution of the coating and the active drug contained in the cores in the proximal part of the small intestine, it also will allow some diffusion of water of gastric juice through the enteric coating into the cores, during the time the dosage form resides in the stomach before it is emptied into the small intestine. The diffused water of gastric juice will dissolve parts of the core in the close proximity of the enteric coating layer and there form an alkaline solution inside the coated dosage form. The alkaline solution will interfere with the enteric coating and eventually dissolve it.

An enteric coated dosage form of omeprazole was reported by Pilbrant and Cederberg, in the above cited Scand. J. Gastroenterology 1985; 20 (suppl. 108) p. 113–120. The publication describes a conventional enteric coated dosage form and states that it has an acceptable storage stability—for clinical studies. It was later found that the stability of this dosage form was insufficient during long-term storage required for a marketed pharmaceutical dosage form.

If a conventional formulation of omeprazole is made, the stability is not satisfactory, particularly in resistance to humidity, and special moisture-proof packing has been adopted to minimize the troubles. However, this provides no satisfactory solution to the problems in today's drug distribution system, and also leads to increased costs. Under the circumstances, there has been a demand for the development of new enteric preparations of omeprazole with better stability.

In DE-A1-No. 3046 559 a way to coat a dosage form is described. First the dosage form is coated with a water insoluble layer containing microcrystalline cellulose and then with a second enteric coating with the aim to achieve a dosage form which releases the active drug in the colon. This method of preparation will not give the desired release of omeprazole in the small intestine.

U.S. Pat. No. 2,540,979 describes an enteric coated oral dosage form, where the enteric coating is combined with a second and/or first coating of a water insoluble "wax" layer. This method of preparation is not applicable on cores containing omeprazole since direct contact between substances such as cellulose acetate phthalate (CAP) and omeprazole causes degradation and discolouration of omeprazole.

DE-B2-No. 23 36 218 describes a method to produce a dialysis membrane consisting of a mixture of one or more conventional enteric coating polymers and one or more insoluble cellulose derivatives. Such a membrane will not give a proper protection of omeprazole in gastric juice.

DE-A1-No. 204 363 describes a three-layer coating procedure. The first layer is soluble in gastric but is insoluble in intestinal juice. The second is water soluble regardless of pH and the third layer is an enteric coating. This preparation as well as the preparation described in DE-A1-No. 1 617 615 result in a dosage form which is not dissolved in gastric juice and which only dissolves slowly in intestinal juice. Such preparations cannot be used for omeprazole, where a rapid release of the drug in the small intestine is needed.

DE-A1 No. 12 04 363 describes coating with three layers to achieve release of a drug in the ileum, an aim which is outside the scope of the present invention.

GB-A-No. 1 485 676 describes a way to obtain a preparation, which effervesces in the small intestine, by enteric coating a core containing the active drug and an effervescing system such as a combination of carbonate and/or bicarbonate salt and a pharmaceutically acceptable acid. The formulation cannot be adopted for a pharmaceutical dosage form containing omeprazole, as the presence of an acid in contact with omeprazole in the cores would give a result that omeprazole was degraded.

WO No. 85/03436 describes a pharmaceutical preparation, wherein cores containing active drugs mixted with for instance buffering components such as sodium dihydrogenphosphate with the aim of maintaining a constant pH and a constant rate of diffusion, are coated with a first coating which controls the diffusion. This formulation cannot be adopted for omeprazole where a rapid release in the small intestive is wanted. Direct application of an enteric coating onto the cores would also adversely influence the storage stability of such dosage forms containing omeprazole.

OUTLINE OF THE INVENTION

The object of the present invention is to provide an enteric coated dosage form of omeprazole, which is resistant to dissolution in acid media and which dissolves rapidly in neutral to alkaline media and which has a good stability during long-term storage. The new dosage form is characterized in the following way. Cores containing omeprazole mixed with alkaline compounds or an alkaline salt of omeprazole optionally mixed with an alkaline compound are coated with two or more layers, whereby the first layer/layers is/are soluble in water o rapidly disintegrating in water and consist(s) of non-acidic, otherwise inert pharmaceutically acceptable substances. This/these first layer/layers separates/separate the alkaline core material from the outer layer, which is an enteric coating. The final, enteric coated dosage form is treated in a suitable way to reduce the water content to a very low level in order to obtain a good stability of the dosage form during long-term storage.

DETAILED DESCRIPTION OF THE INVENTION

Cores

Omeprazole is mixed with inert, preferably water soluble, conventional pharmaceutical constituents to obtain the preferred concentration of omeprazole in the final mixture and with an alkaline reacting, otherwise inert, pharmaceutically acceptable substance (or substances), which creates a "micro-pH" around each omeprazole particle of not less than pH=7, preferably not less than pH=8, when water is adsorbed to the particles of the mixture or when water is added in small amounts to the mixture. Such substances can be chosen among, but are not restricted to substances such as the sodium, potassium, calcium, magnesium and aluminium salts of phosphoric acid, carbonic acid, citric acid or other suitable weak inorganic or organic acids; substances normally used in antacid preparations such as aluminium, calcium and magnesium hydroxides; magnesium oxide or composite substances, such as $Al_2O_3.6MgO.CO_2.12H_2O$, $(Mg_6Al_2(OH)_{16}CO_3.4H_2O)$, $MgO.Al_2O_3.2SiO_2.nH_2O$ or similar compounds; organic pH-buffering substances such as trihydroxymethylaminomethane or other similar, pharmaceutically acceptable pH-buffering substances. The stabilizing, high pH-value in the powder mixture can also be achieved by using an alkaline reacting salt of omeprazole such as the sodium, potassium, magnesium, calcium etc. salts of omeprazole, which are described in e.g. EP-A2-No. 124 495, either alone or in combination with a conventional buffering substance as previously described.

The powder mixture is then formulated into small beads i.e. pellets, tablets, hard gelatine or soft gelatine capsules by conventional pharmaceutical procedures.

The pellets, tablets or gelatin capsules are used as cores for further processing.

Separating layer

The omeprazole containing alkaline reacting cores must be separated from the enteric coating polymer(s) containing free carboxyl groups, which otherwise causes degradation/discolouration of omeprazole during the coating process or during storage. The subcoating layer, in the following defined as the separating layer, also serves as a pH-buffering zone in which hydrogen ions diffusing from the outside in towards the alkaline core can react with hydroxyl ions diffusing from the alkaline core towards the surface of the coated articles. The pH-buffering properties of the separating layer can be further strengthened by introducing in the layer substances chosen from a group of compounds usually used in antacid formulations such as, for instance, magnesium oxide, hydroxide or carbonate, aluminium or calcium hydroxide, carbonate or silicate; composite aluminium/magnesium compounds such as, for instance $Al_2O_3.6MgO.CO_2 12H_2O$, $(Mg_6Al_2(OH)_{1-6}CO_3.4H_2O)$, $MgO.Al_2O_3.2SiO_2.nH_2O$ or similar compounds; or other pharmaceutically acceptable pH-buffering compounds such as, for instance the sodium, potassium, calcium, magnesium and aluminium salts of phosphoric, citric or other suitable, weak, inorganic or organic acids.

The separating layer consists of one or more water soluble inert layer, optionally containing pH-buffering compounds.

The separating layer(s) can be applied to the cores—pellets or tablets—by conventional coating procedures in a suitable coating pan or in a fluidized bed apparatus using water and/or conventional organic solvents for the coating solution. The material for the separating layer is chosen among the pharmaceutically acceptable, water soluble, inert compounds or polymers used for film-coating applications such as, for instance sugar, polyethylene glycol, polyvinylpyrroline, polyvinyl alcohol, hydroxypropyl cellulose, methylcellulose, hydroxymethyl cellulose, hydroxypropyl methylcellulose, polyvinyl acetal diethylaminoacetate or the like. The thickness of the separating layer is not less than 2 $\mu$m, for small spherical pellets preferably not less than 4 $\mu$m, for tablets preferably not less than 10 $\mu$m.

In the case of tablets another method to apply the coating can be performed by the drycoating technique. First a tablet containing omeprazole is compressed as described above. Around this tablet a layer is compressed using a suitable tableting machine. The outer, separating layer, consists of pharmaceutically acceptable, in water soluble or in water rapidly disintegrating tablet excipients. The separating layer has a thickness of not less than 1 mm. Ordinary plasticizers colorants, pigments, titanium dioxide, talc and other additives may also be included into the separating layer.

In case of gelatin capsules the gelatin capsule itself serves as separating layer.

Enteric coating layer

The eneric coating layer is applied on to the subcoated cores by conventional coating techniques such as, for instance, pan coating or fluidized bed coating using solutions of polymers in water and/or suitable organic solvents or by using latex suspensions of said polymers. As enteric coating polymers can be used, for example, cellulose acetate phthalate, hydroxypropyl methylcellulose phthalate, polyvinyl acetate phthalate, carboxymethylethylcellulose, co-polymerized methacrylic acid/methacrylic acid methyl esters such as, for instance, compounds known under the trade name Eudragit ®L 12,5 or Eudragit ®L 100 (Röhm Pharma), or similar compounds used to obtain enteric coatings. The enteric coating can also be applied using water-based polymer dispersions, e.g. Aquateric ® (FMC Corporation), Eudragit ®L100-55 (Röhm Pharma), Coating CE 5142 (BASF). The enteric coating layer can optionally contain a pharmaceutically acceptable plasticizer such as, for instance, cetanol, triacetin, citric acid esters such as, for instance, those known under the trade name Citroflex ® (Pfizer), phthalic acid esters, dibutyl succinate or similar plasticizers. The amount of plasticizer is usually optimized for each enteric coating polymer(s) and is usually in the range of 1–20% of the enteric coating polymer(s). Dispersants such as talc, colorants and pigments may also be included into the enteric coating layer.

Thus, the special preparation according to the invention consists of cores containing omeprazole mixed with an alkaline reacting compound or cores containing an alkaline salt of omeprazole optionally mixed with an alkaline reacting compound. The alkaline reacting core material and/or alkaline salt of the active ingredient, omeprazole, enhance the stability of omeprazole. The cores suspended in water forms a solution or a suspension which has a pH, which is higher than that of a solution in which the polymer used for enteric coating is just soluble. The cores are coated with an inert reacting water soluble or in water rapidly disintegrating coating, optionally containing a pH-buffering substance, which separates the alkaline cores from the enteric coating. Without this separating layer the resistance towards gastric juice would be too short and/or the storage stability of the dosage form would be unacceptably short. The sub-coated dosage form is finally coated with an enteric coating rendering the dosage form insoluble in acid media, but rapidly disintegrating/dissolving in neutral to alkaline media such as, for instance the liquids present in the proximal part of the small intestine, the site where dissolution is wanted.

Final dosage form

The final dosage form is either an enteric coated tablet or capsule or in the case of enteric coated pellets, pellets dispensed in hard gelatin capsules or sachets or pellets formulated into tablets. It is essential for the long term stability during storage that the water content of the final dosage form containing omeprazole (enteric coated tablets, capsules or pellets) is kept low, preferably not more than 1.5% by weight. As a consequence the final package containing hard gelatin capsules filled with enteric coated pellets preferably also contain a desiccant, which reduces the water content of the gelatin shell to a level where the water content of the enteric coated pellets filled in the capsules does not exceed 1.5% by weight.

Process

A process for the manufacturer of the oral dosage form represents a further aspect of the invention. After the forming of the cores the cores are first coated with the separating layer and then with the enteric coating layer. The coating is carried out as described above.

The preparation according to the invention is especially advantageous in reducing gastric acid secretion and/or providing a gastrointestinal cytoprotective effect. It is administered one to several times a day. The typical daily dose of the active substance varies and will depend on various factors such as the individual requirements of the patients, the mode of administration and disease. In general the daily dose will be in the range of 1–100 mg of omeprazole. A method for the treatment of such conditions using the novel oral dosage form respresents a further aspect of the invention.

The invention is described in detail in the following examples:

EXAMPLES

Example 1

The effect of different magnesium compounds was evaluated in the form of enteric coated tablets. Tablet cores were first made by known techniques according to the formulations listed in Table 1, followed by application of separating layers and enteric coating layers as shown in Table 2.

TABLE 1

| Formulations No. | Formulations for the tablet cores (mg) | | | | | | |
|---|---|---|---|---|---|---|---|
| | 1 | 2 | 3 | 4 | 5 | 6 | 7 |
| Omeprazol | 15.0 | 15.0 | 15.0 | 15.0 | 15.0 | 15.0 | 15.0 |
| Lactose | 134.0 | 119.0 | 119.0 | 119.0 | 118.8 | 118.5 | 119.0 |
| Hydroxypropyl cellulose (low substitution | 5.0 | 5.0 | 5.0 | 5.0 | 5.0 | 5.0 | 5.0 |
| Hydroxypropyl cellulose | 1.0 | 1.0 | 1.0 | 1.0 | 1.0 | 1.0 | 1.0 |
| Talc | 5.0 | 5.0 | 5.0 | 5.0 | 5.0 | 5.0 | 5.0 |
| Na$_2$HPO$_4$ | — | 15.0 | — | — | 0.2 | — | — |
| Na lauryl sulfate | — | — | — | — | — | 0.5 | — |
| MgO | — | — | 15.0 | — | — | — | — |
| Mg(OH)$_2$ | — | — | — | 15.0 | 15.0 | 15.0 | — |
| Synthetic hydrotalcite [Al$_2$O$_3$.6MgO.CO$_2$.12H$_2$O] | — | — | — | — | — | — | 15.0 |
| Total | 160.0 | 160.0 | 160.0 | 160.0 | 160.0 | 160.0 | 160.0 |

TABLE 2

| Formulation No. | Formulations for coatings (mg) | | | |
|---|---|---|---|---|
| | I | II | III | IV |
| Separating layer (inner): | | | | |
| Hydroxypropyl cellulose | — | 2.0 | 2.0 | 2.0 |
| Magnesium hydroxide | — | — | 0.3 | — |
| Synthetic hydrotalcite | — | — | — | 0.3 |
| Separating layer (outer): | | | | |
| Hydroxypropyl cellulose | — | 2.0 | 2.0 | 2.0 |
| Enteric coating layer: | | | | |
| Hydroxypropyl methylcellulose phthalate | 7.0 | 7.0 | 7.0 | 7.0 |
| Cetyl alcohol | 0.5 | 0.5 | 0.5 | 0.5 |

The tablets thus obtained were stored in open form under so called accelerated conditions, that is 40° C., and 75% relative humidity, and the changes in appearance with the passage of time were observed. Storage for six months under these conditions corresponds to storage at normal temperature for three years. This means that high stability sufficient for paractical use may be assured if a drug remains intact for about one week under the mentioned conditions. The result is summerized in Table 3. As may be seen from the table, a remarkable stabilizing effect is achieved when a magnesium compound is contained in the inner separating layer.

TABLE 3

Stabilizing Effect (Appearance of Preparations)

| Coating Layer | Core material | | | | | | |
|---|---|---|---|---|---|---|---|
| | 1 | 2 | 3 | 4 | 5 | 6 | 7 |
| I  At the start | C | A | A | A | A | A | A |
| 60° C.; after 7 days | E | D | C | C | C | C | D |
| 40° C.; 75% RH; after 7 days | F | E | B | B | B | B | E |
| II  At the start | A | A | A | A | A | A | A |
| 60° C.; after 7 days | E | B | A | A | A | A | C |
| 40° C.; 75% RH; after 7 days | E | D | A | A | A | A | D |
| III  At the start | A | A | A | A | A | A | |
| 60° C.; after 15 days | B | A | A | A | A | A | |
| 40° C.; after 30 days | A | A | A | A | A | A | |
| 40° C.; 75% RH; after 15 days | B | A | A | A | A | A | |
| IV  At the start | A | A | A | A | A | A | |
| 60° C.; after 15 days | B | A | A | A | A | A | |
| 40° C.; after 30 days | A | A | A | A | A | A | |
| 40° C.; 75% RH; after 15 days | B | A | A | A | A | A | |

A: white,
B: brownish white,
C: faint brown,
D: light brown,
E: brown,
F: deep brown.

All the samples evaluated as A (white) in the above table showed no descoloration even on split surfaces. The samples evaluated as B (brownish white) showed little change in appearance, but some discoloration was observed on split surfaces.

Table 4 shows the result of a stability test on the omeprazole preparation according to Example 1 (Formulation No 4-IV). The formulation was stored in a closed glass bottle at room temperature for the indicated period of time. This clearly demonstrates that preparations with unusually high stability were obtained.

TABLE 4

Stability of enteric coated omeprazole preparations (Tablets of Formulation No. 4-IV)

| Storage Period | Appearance | Omeprazole Content (%) |
|---|---|---|
| At the start of test | White | 100.0 |
| 1 year at room temperature | White | 99.9 |
| 2 years at room temperature | White | 100.0 |

Example 2

| | Uncoated pellets | |
|---|---|---|
| I | Mannitol powder | 16 150 g |
| | Lactose anhydrous | 800 g |
| | Hydroxypropyl cellulose | 600 g |
| | Microcrystalline cellulose | 400 g |
| II | Omeprazole | 2 000 g |
| | Sodium lauryl sulphate | 50 g |
| | Disodium hydrogen phosphate | 80 g |
| | Distilled water | 4 400 g |

The dry ingredients (I) were premixed in a mixer. Addition of a granulation liquid (II) containing suspended omeprazole was made and the mass was wet-mixed to a proper consistency. The wet mass was pressed through an extruder and spheronized to pellets. The pellets were dried and classified into suitable particle size ranges.

| | Subcoated pellets | |
|---|---|---|
| II | Uncoated omeprazole pellets | 6 000 g |
| | Hydroxypropyl methylcellulose | 240 g |
| | Distilled water | 4 800 g |

The polymer solution (III) was sprayed on the uncoated pellets in a fluidized bed apparatus. The spray guns were placed above the fluidized bed.

| | Enteric-coated pellets | |
|---|---|---|
| IV | Subcoated pellets | 500 g |
| | Hydroxypropyl methylcellulose phthalate | 57 g |
| | Cetyl alcohol | 3 g |
| | Acetone | 540 g |
| | Ethanol | 231 g |

The polymer solution (IV) was sprayed on the subcoated pellets in a fluidized bed apparatus with spray guns placed above the bed. After drying to a water content of 0.5% the enteric coated pellets were classified and filled into hard gelatin capsules in an amount of 225 mg, corresponding to 20 mg of omeprazole. 30 capsules were packed in tight containers together with a desiccant.

Example 3

This example illustrates that a variety of polymers can be used for subcoating, e.g. hydroxypropyl methylcellulose, hydroxypropyl cellulose, polyvinylpyrrolidone, polyethylene glycol, polyvinyl alcohols.

| | Uncoated pellets | |
|---|---|---|
| I | Mannitol powder | 1 620 g |
| | Lactose anhydrous | 80 g |
| | Hydroxypropyl cellulose | 60 g |
| | Microcrystalline cellulose | 40 g |
| II | Omeprazole | 200 g |
| | Sodium lauryl sulphate | 1.0 g |
| | Disodium hydrogen phosphate | 9.3 g |
| | Distilled water | 515 g |

The uncoated pellets were prepared as described in Example 2.

| | Subcoated pellets | |
|---|---|---|
| III | Uncoated omeprazole pellets | 500 g |
| | Polyvinylpyrrolidone | 20 g |
| | Ethanol | 400 g |

The subcoated pellets were prepared as described in Example 2.

| | Enteric-coated pellets | |
|---|---|---|
| IV | Subcoated pellets | 500 g |
| | Hydroxypropyl methylcellulose phthalate | 45 g |
| | Cetyl alcohol | 5 g |
| | Acetone | 219 g |

-continued

| Enteric-coated pellets | |
|---|---|
| Ethanol | 680 g |

The enteric-coated pellets were prepared as described in Example 2.

Example 4

| | Uncoated pellets | |
|---|---|---|
| I | Mannitol powder | 1 610 g |
| | Lactose anhydrous | 80 g |
| | Hydroxypropyl cellulose | 60 g |
| | Microcrystalline cellulose | 40 g |
| II | Omeprazole | 200 g |
| | Pluronic F68 | 10 g |
| | Disodium hydrogen phosphate | 24 g |
| | Distilled water | 450 g |

The uncoated pellets were prepared as described in Example 2.

| | Subcoated pellets | |
|---|---|---|
| III | Uncoated pellets | 500 g |
| | Polyvinylpyrrolidone | 30 g |
| | Ethanol | 400 g |

The subcoated pellets were prepared as described in Example 2.

| | Enteric coated pellets | |
|---|---|---|
| IV | Subcoated pellets | 500 g |
| | Hydroxypropyl methylcellulose phthalate | 45 g |
| | Cetyl alcohol | 5 g |
| | Methylene chloride | 371 g |
| | Ethanol | 680 g |

The enteric coated pellets were prepared as described in Example 2.

Example 5

This example illustrates that a variety of polymers can be used as enteric coating material e.g. cellulose acetate phthalate, poly-(vinyl acetate/vinyl alcohol phthalate), hydroxypropyl methylcellulose phthalate, poly-(methacrylic acid/methacrylic acid methyl esters), poly-(acrylic acid/methacrylic acid methyl esters). The polymers can be applied with/without plasticizer, e.g. polyethylene glycols, triacetin, dimethyl polysiloxan, Citroflex®, cetyl alcohol, stearyl alcohol, diethyl phthalate.

Enteric-coated pellets can also be manufactured from water-based polymer dispersions, e.g. Aquateric (FMC Corporation), Eudragit®L 100-55, Coating CE 5142 (BASF).

| | Uncoated pellets | |
|---|---|---|
| I | Lactose powder | 277 g |
| | Lactose anhydrous | 118 g |
| | Hydroxypropyl cellulose | 25 g |
| | Colloidal silica | 25 g |
| II | Omeprazole | 50 g |
| | Sodium lauryl sulphate | 5 g |
| | Disodium hydrogen phosphate | 2 g |
| | Sodium dihydrogen phosphate | 0.1 g |

| Uncoated pellets | |
|---|---|
| Distilled water | 170 g |

The uncoated pellets were prepared as described above.

Subcoated pellets

The uncoated pellets were subcoated as described in Example 2.

| | Enteric coated pellets | |
|---|---|---|
| III | Subcoated pellets | 500 g |
| | Eudragit L 100 | 45 g |
| | Stearyl alcohol | 4.5 g |
| | Ethanol | 1 320 g |

The enteric coated pellets were prepared as described above.

Example 6

Formulations with the sodium salt of omeprazole.

| | Uncoated pellets | |
|---|---|---|
| I | Omeprazole sodium salt | 339 g |
| | Mannitol powder | 2 422 g |
| | Lactose anhydrous | 120 g |
| | Hydroxypropyl cellulose | 90 g |
| | Microcrystalline cellulose | 60 g |
| II | Sodium lauryl sulphate | 7 g |
| | Distilled water | 650 g |

The preparation was made as described in Example 2 with the exception that the omeprazole sodium salt was added together with the other ingredients in mixture I.

| | Subcoated pellets | |
|---|---|---|
| III | Uncoated pellets | 500 g |
| | Hydroxypropyl methylcellulose | 20 g |
| | Aluminium hydroxide/magnesium carbonate | 4 g |
| | Distilled water | 400 g |
| IV | Pellets subcoated with III | 500 g |
| | Hydroxypropyl methylcellulose | 20 g |
| | Distilled water | 400 g |

The two subcoat layers, III and IV, were applied to the uncoated pellets in a fluidized bed apparatus in consecutive order as previously described.

| | Enteric coated pellets | |
|---|---|---|
| V | Subcoated pellets | 500 g |
| | Hydroxypropyl methylcellulose phthalate | 57 g |
| | Cetyl alcohol | 3 g |
| | Acetone | 540 g |
| | Ethanol | 231 g |

The preparation of enteric coated pellets was performed as described in Example 2.

Example 7 and 8

Formulations with the magnesium salt of omeprazole.

| Uncoated pellets | | Example No | |
|---|---|---|---|
| | | 7 | 8 |
| I | Omeprazole magnesium salt | 222 g | 222 g |
| | Mannitol powder | 1 673 g | 1 473 g |
| | Microcrystalline cellulose | 100 g | 100 g |
| | Magnesium hydroxide | — | 200 g |
| II | Sodium lauryl sulphate | 5 g | 5 g |
| | Distilled water | 500 g | 375 g |

The preparation was made as described in Example 2 with the exception that the omeprazole magnesium salt was added together with the other ingredients in mixture I.

| Subcoated pellets | | Example 7 and 8 |
|---|---|---|
| III | Uncoated pellets | 500 g |
| | Hydroxypropyl methylcellulose | 20 g |
| | Distilled water | 400 g |

The pellets were prepared as described in Example 2.

| Enteric coated pellets | | Examples 7 and 8 |
|---|---|---|
| IV | Subcoated pellets | 500 g |
| | Hydroxypropyl methylcellulose phthalate | 57 g |
| | Cetyl alcohol | 3 g |
| | Acetone | 540 g |
| | Ethanol | 231 g |

The enteric coated pellets were prepared as described in Example 2.

Example 9 and 10

Manufacture of tablets.

| Tablet cores | | Examples No | |
|---|---|---|---|
| | | 9 | 10 |
| I | Omeprazole | 400 g | — |
| | Omeprazole sodium salt, corresponding to omeprazole 400 g | — | 426 g |
| | Lactose, anhydrous | 1 420 g | 1 409 g |
| | Polyvinylpyrrolidone, crosslinked | 100 g | 100 g |
| | Sodium carbonate, anhydrous | 15 g | — |
| II | Methyl cellulose | 12 g | 12 g |
| | Distilled water | 200 g | 200 g |
| | Magnesium stearate | 30 g | 30 g |

The powder mixture I was carefully homogenized and granulated by the solution II. The wet mass was dried in a fluidized bed dryer using an inlet air temperature of +50° C. for 30 minutes. The dried mixture was then forced through a sieve with an apperture of 0.5 mm. After mixing with magnesium stearate the granulate was tableted on a tableting machine using 6 mm punches. The tablet weight was 100 mg.

Subcoating

The tablets containing omeprazole were subcoated with approximately 10% by weight of hydroxypropyl methylcellulose from a water solution using a perforated coating pan apparatus.

The tablets containing omeprazole sodium salt were subcoated using the dry coating technique. A tablet granulate containing

| Lactose anhydrous | 4 000 g |
|---|---|
| Polyvinylpyrrolidone, (PVP) | 180 g |
| Ethanol 95% | 420 g |
| Magnesium stearate | 42 g | was prepared in the following way. The lactose was granulated with a solution of PVP in ethanol and dried. After drying magnesium stearate was admixed.

The granulate mass was dry coated around the tablet cores of example 9 using a Manesty Dry Cota ® tableting machine. The tablet weight of the dry coated tablets was 475 mg. Each tablet contained 20 mg of omeprazole.

Enteric coating

The subcoated tablets obtained above were enteric coated using the same coating solution:

| Hydroxypropyl methylcellulose phthalate | 1 500 g |
|---|---|
| Cetyl alcohol | 105 g |
| Methylene chloride | 15 000 g |
| Isopropanol | 15 000 g |
| Distilled water | 3 150 g |

The coating was applied in a perforated coating pan apparatus. An approximate amount of one kg of coating solution was applied for each kg of tablets.

COMPARATIVE EXAMPLES

Examples I, II and III

These examples illustrative that the buffer salt used effects the enteric-coated omeprazole pellets properties when the sub-coating layer is absent. A high amount of buffer salt is needed in order to obtain a long shelf life for the product. At the same time this type of pellets shows inferior acid resistance properties. C.f. also the Example 4 above.

| Uncoated pellets | | Examples No | | |
|---|---|---|---|---|
| | | I | II | III |
| I | Mannitol powder | 1 610 g | 1 610 g | 1 610 g |
| | Lactose anhydrous | 80 g | 80 g | 80 g |
| | Hydroxypropyl cellulose | 60 g | 60 g | 60 g |
| | Microcrystalline cellulose | 40 g | 40 g | 40 g |
| II | Omeprazole | 200 g | 200 g | 200 g |
| | Pluronic F68 | 10 g | 10 g | 10 g |
| | Disodium hydrogen phosphate | 2 g | 8 g | 24 g |
| | Distilled water | 450 g | 450 g | 450 g |

The uncoated pellets were prepared as described in Example 2 above.

| Enteric coated pellets | |
|---|---|
| Uncoated pellets | 500 g |
| Hydroxypropyl methylcellulose | 45 g |

| Enteric coated pellets | | |
|---|---|---|
| III | phthalate | |
| | Cetyl alcohol | 5 g |
| | Methylene chloride | 371 g |
| | Ethanol | 680 g |

The coated pellets were prepared as described in Example 2 above.

Example IV

This formulation is the same as in Example 6 above, but no subcoating layer was used.

| Uncoated pellets | | |
|---|---|---|
| I | Omeprazole sodium salt | 339 g |
| | Mannitol powder | 2 422 g |
| | Lactose anhydrous | 120 g |
| | Hydroxypropyl cellulose | 90 g |
| | Microcrystalline cellulose | 60 g |
| II | Sodium lauryl sulphate | 7 g |
| | Distilled water | 650 g |

The preparation was made as described in Example 6.

| Enteric-coated pellets | | |
|---|---|---|
| III | Uncoated pellets | 500 g |
| | Hydroxypropyl methylcellulose phthalate | 57 g |
| | Cetyl alcohol | 3 g |
| | Acetone | 540 g |
| | Ethanol | 231 g |

The enteric coated pellets were prepared as described in Example 2.

Example V

This formulation is the same as in Example 8 above, but no subcoating layer was used.

| Uncoated pellets | | |
|---|---|---|
| I | Omeprazole magnesium salt | 222 g |
| | Mannitol powder | 1 473 g |
| | Microcrystalline cellulose | 100 g |
| | Magnesium hydroxide | 200 g |
| II | Sodium lauryl sulphate | 5 g |
| | Distilled water | 375 g |

The preparation was made as described in Example 8.

| Enteric coated pellets | | |
|---|---|---|
| III | Uncoated pellets | 500 g |
| | Hydroxypropyl methylcellulose phthalate | 57 g |
| | Cetyl alcohol | 3 g |
| | Acetone | 540 g |
| | Ethanol | 231 g |

The pellets were prepared as described in Example 2 above.

Properties of the enteric coated pellets

For the preparations according to Examples 2–8 and comparative Examples I–V above one or both of the following studies have been performed.

Acid resistance

The following resistance of the formulations was studied in the following way: The formulations were added to gastric fluid USP (without enzyme), 37° C. (paddle) 100 r/min. After 2 hours the actual amount of omeprazole remaining intact in the formulations was determined.

Rate of dissolution in buffer solution

In order to establish the rate of dissolution in the small intestine, the formulations were added to a buffer solution. Buffer solution 37° C., USP dissolution apparatus No 2 (paddle), 100 r/min. After 10 or 30 minutes the amount of omeprazole dissolved was determined. The results are presented in the following Table 5.

| Example No | Omeprazole content mg/g | Acid resistance, amount intact omeprazole (%) after 2 hours | % dissolved omeprazole at different pH:s and after 10 or 30 min | | |
|---|---|---|---|---|---|
| | | | % | pH | min |
| 2 | 89.2 | 95 | 100 | 6.8 | 10 |
| 3 | 90 | 96 | 91 | 6.0 | 10 |
| 4 | 88 | 89 | (*) | | |
| 5 | 82 | 93 | 70 | 7.5 | 30 |
| 6 | 81.3 | 87 | 93 | 6.8 | 10 |
| 7 | 91 | 95 | (**) | | |
| 8 | 89 | 98 | (**) | | |
| I | 93 | 97 | (*) | | |
| II | 92 | 94 | (*) | | |
| III | 94 | 58 | (*) | | |
| IV | 86.5 | 4 | | | |
| V | 91 | 93 | (**) | | |

(*) The stability of the formulation was studied during storage in glass bottles also containing a desiccant device. After one month storage at +50° C. the formulation according to Example 4 was virtually intact with no change in appearance or physicochemical characteristics. Pellets according to Example I and II turned brown due to degradation, while the pellets according to Example III retained to original white colour.

(**) The formulations according to Examples 7 and 8 were white and not affected by the coating process. The enteric coated pellets according to Example V, where the enteric coating was applied directly on the cores according to Example 8, was discoloured already during the enteric coating process.

Further comparative test

This example demonstrates the effect of the moisture content of the preparations according to the invention on storage stability.

The stability of omeprazole pellets according to the invention was compared with that of omeprazole pellets with higher water content. Omeprazole pellets were prepared according to the invention with a water content of 1%. Two other portions of the same formulation were conditioned to a water content of 2% and 5% respectively. The three formulations, packed in tight containers not contining a desiccant, were stored for one month at +50° C. After this time the packages were opened and the pellets were assayed for the amount of omeprazole by HPLC. The formulation according to the invention had an omeprazole content of 98.5% of the initial value. The other two formulations with a water content of 2 and 5% respectively were virtually totally degraded and had only trace amounts of intact omeprazole.

DISCUSSION

From the results given in Table 5 it can be seen that formulations containing omeprazole with acceptable acid resistance can be prepared by using a conventional enteric coating technique (see for instance Examples I, II and V). However, it is also obvious that the storage stability of the formulations according to Examples I, II and V is not acceptable, since a discolouration, showing a degradation of omeprazole, occours during short storage at an elevated storage temperature (Examples I and II) or already during the enteric coating process (Example V).

If the amount of alkaline substances in the cores is increased to a level where omeprazole has an acceptable storage stability (Example III) or if an alkaline reacting salt of omeprazole is used in the preparation of the cores (Example IV), then, without the separating layer of the invention, the resistance to dissolution in acid media becomes unacceptably low and much or all of the active substance will degrade already in the stomach and thus, it has no effect on the gastric acid secretion.

When the preparation is carried out according to the inventon as for instance in Example 4, a good resistance towards gastric juice as well as a good stability during long-term storage is obtained. This is in contrast with the formulations in Examples I, II and III where either an acceptable acid resistance or an acceptable storage stability can be achieved—but not both. The same comparison can be made between the formulations according to Examples 7 and 8 according to the invention and the formulation according to Example V, where the separating layer was omitted. Examples 7 and 8 differ in that a buffering substance, magnesium hydroxide, has been included in the cores of Example 8. This further improves the acid resistance as well as the storage stability of Example 8 in comparison with Example 7.

The further comparative test shows the great importance of a low water content in the preparations.

Thus in order to prepare pharmaceutical formulations of omeprazole for oral use, which exert good stability during long-term storage as well as good stability during the residence in the stomach after administration, the preparation is made in the following way:

(a) Omeprazole together with an alkaline reacting compound or compounds or an alkaline reacting salt of omeprazole optionally mixed with alkaline reacting compound are included in the core material.

(b) The core material is subcoated with one or more inert, in water soluble or in water rapidly disintegrating layers, which separate the alkaline reacting core from the enteric coating. The subcoating layer may optionally contain pH-buffering compounds.

(c) The subcoated cores are coated with an acid insoluble enteric coating, optionally containing plasticizers.

Biopharmaceutical studies

The hard gelatin capsules according to Example 2 were administered to 12 healthy, young male volunteers in the following way:

The volunteers came to the laboratory in the morning after having abstained from food since 10 p.m. the night preceeding the experimental day. A zero time blood sample was taken. One omeprazole capsule according to Example 2 was administered together with 150 ml of tap water. Further blood samples were taken during the day.

In another experiment the same volunteers were administered 20 mg of omeprazole in the form of a suspension of micronized omeprazole in a sodium bicarbonate water solution. In order to reduce the degradation of omeprazole in the stomach to a minimum, sodium bicarbonate solution was given to the subjects just before the administration of the omeprazole suspension and at further four times with a 10-minutes interval after the drug intake. The concentration of omeprazole in blood plasma was assayed by high pressure liquid chromatography (Persson, Lagerström and Grundevik. Scand J Gastroenterol 1985, 20, (suppl 108), 71–77. The mean plasma concentrations are given in Table 6.

TABLE 6

The plasma concentrations ($\mu$mol/l) after 20 mg single oral doses of omeprazole given as hard gelatin capsules according to Example 2 and as a suspension of micronized omeprazole in sodium bicarbonate solution.

| Time (min) | Capsules | Suspension |
|---|---|---|
| 10 | | 0.84 |
| 20 | | 0.90 |
| 30 | 0.03 | 0.84 |
| 45 | | 0.64 |
| 60 | 0.22 | 0.44 |
| 90 | 0.36 | 0.24 |
| 120 | 0.39 | 0.13 |
| 150 | 0.29 | |
| 180 | 0.20 | 0.04 |
| 210 | 0.10 | |
| 240 | 0.05 | 0.01 |
| 300 | 0.02 | 0 |
| 360 | 0.01 | |
| 420 | 0 | |

Although the plasma concentration peak at different times, the two formulations are bioequivalent. The mean relative bioavailability of the capsules in comparision with the suspension was 85%+23% (S.D.). The comparison was based on the total area under individual plasma concentration versus time curves.

Thus, by preparing capsules according to the invention it is possible to obtain a preparation with the same bioavailability as a suspension containing the same amount of micronized active compound. It is, however, to be noticed that when the suspension is administered, the patients must also be given sodium bicarbonate solution frequently in order to minimize pre-absorption degradation of omeprazole in the stomach.

We claim:

1. An oral pharmaceutical preparation comprising
   (a) a core region comprising an effective amount of a material selected from the group consisting of omeprazole plus an alkaline reacting compound, an alkaline omeprazole salt plus an alkaline reacting compound and an alkaline omeprazole salt alone;
   (b) an inert subcoating which is soluble or rapidly disintegrating in water disposed on said core region, said subcoating comprising one or more layers of materials selected from among tablet excipients and polymeric film-forming compounds; and
   (c) an outer layer disposed on said subcoating comprising an enteric coating.

2. A preparation according to claim 1 wherein the subcoating layer comprises one or more of magnesium oxide, magnesium hydroxide or composite substance [$Al_2O_3.6MgO.CO_2.12H_2O$ or $MgO.Al_2O_3.2SiO_2.nH_2O$], wherein n is not an integer and less than 2.

3. A preparation according to claim 1 wherein the subcoating comprises two or more sub-layers.

4. A preparation according to claim 3 wherein the subcoating comprises hydroxypropyl methylcellulose, hydroxypropyl cellulose or polyvinylpyrrolidone.

5. A preparation according to claim 1 wherein the alkaline core comprises omeprazole and pH-buffering alkaline compound rendering to the micro-environment of omeprazole a pH of 7–12.

6. A preparation according to claim 5 wherein the alkaline compound comprises one or more of magnesium oxide, hydroxide or carbonate, aluminium hydroxide, aluminium, calcium, sodium or potassium carbonate, phosphate or citrate, the composite aluminium/-magnesium compounds $Al_2O_3.6MgO.CO_2.12H_2O$ or $MgO.Al_2O_3.2SiO_2.nH_2O$, where n is not an integer and less than 2.

7. A preparation according to claim 1, wherein the core region comprises a salt of omeprazole selected from along the sodium, potassium, magnesium, calcium and ammonium salts.

8. A preparation according to claim 1 wherein the enteric coating comprises hydroxypropyl methylcellulose pthalate, cellulose acetate phthalate, co-polymerized methacrylic acid/methacrylic acid methyl ester or polyvinyl acetate phthalate, optionally containing a plasticizer.

9. A preparation according to claim 1 wherein the water content of the final dosage form containing omeprazole does not exceed 1.5% by weight.

10. A method for the treatment of gastrointestinal disease comprising administering to a host in need of such treatment a therapeutically effective amount of a preparation according to claim 1.

11. A preparation according to claim 1, wherein the subcoating further comprises an alkaline buffering compound.

12. A preparation according to claim 1, wherein the core comprises omeprazole and disodium hydrogen phosphate, and the subcoating comprises hydroxy propyl methyl cellulose.

13. A preparation according to claim 1, wherein the alkaline core comprises omeprazole and magnesium hydroxide, the subcoating comprises a layer comprising hydroxypropyl cellulose and synthetic hydrotalcite, and the outer layer comprises hydroxypropyl cellulose.

14. A process for the preparation of an oral pharmaceutical preparation containing omeprazole, comprising
(a) preparing a core comprising an effective amount of a material selected from the group consisting of omeprazole plus an alkaline reacting compound, an alkaline omeprazole salt plus an alkaline reacting compound and an alkaline omeprazole salt alone;
(b) coating the core with one or more layers of an inert subcoating material selected from among tablet excipients and polymeric film-forming compounds to form a subcoated core; and
(c) coating the subcoated core with an enteric coating.

* * * * *

UNITED STATES PATENT AND TRADEMARK OFFICE
CERTIFICATE OF CORRECTION

PATENT NO. : 4,786,505

DATED : November 22, 1988

INVENTOR(S) : Kurt I. Lovgren et al.

It is certified that error appears in the above-identified patent and that said Letters Patent is hereby corrected as shown below:

First page, first column, last line, "4,685,919" should read --4,685,918--;

First page, second column, after "1485676  9/1977  United Kingdom" insert

--0077956  5/1983  European
  862376  3/1961  Great Britain

Other Documents

Developement of an oral formulation of omeprazole
Pilbrant A. and Cederberg C., Department of Pharmaceutics and Medicine, pgs-113-120.--.

Column 1, line 41, after "release" insert --of--;

Column 2, line 45, "204 363" should read --1 204 363--;

Column 4, line 39, "polyvinylpyrroline" should read --polyvinylpyrrolidone--;

Column 6, line 20, "1-100 mg" should read --1-400 mg--;

Column 14, between lines 17 and 19, insert --TABLE 5--;

Column 17, line 11, "along" should read --among--;

UNITED STATES PATENT AND TRADEMARK OFFICE
CERTIFICATE OF CORRECTION

PATENT NO. : 4,786,505
DATED : November 22, 1988
INVENTOR(S) : Kurt I. Lovgren et al.

It is certified that error appears in the above-identified patent and that said Letters Patent is hereby corrected as shown below:

Column 17, line 15, "pthalate" should read -- phthalate --.

Signed and Sealed this

Eighteenth Day of July, 1989

Attest:

DONALD J. QUIGG

Attesting Officer

Commissioner of Patents and Trademarks